United States Patent [19]
Warner et al.

[11] Patent Number: 5,957,969
[45] Date of Patent: *Sep. 28, 1999

[54] TUNABLE MICROWAVE ABLATION CATHETER SYSTEM AND METHOD

[75] Inventors: Glen Grant Warner, Morgan Hill; David Alan Grundy, Fremont; R. Hardwin Mead, Palo Alto, all of Calif.

[73] Assignee: FIDUS Medical Technology Corporation, Fremont, Calif.

[ * ] Notice: This patent is subject to a terminal disclaimer.

[21] Appl. No.: 08/898,712

[22] Filed: Jul. 22, 1997

Related U.S. Application Data

[63] Continuation of application No. 08/300,948, Sep. 6, 1994, Pat. No. 5,693,082, which is a continuation-in-part of application No. 08/062,637, May 14, 1993, Pat. No. 5,364,392, and application No. 08/163,178, Sep. 6, 1994, Pat. No. 5,405,346.

[51] Int. Cl.$^6$ .................................................. A61B 17/39
[52] U.S. Cl. ............................ 607/156; 606/34; 606/42; 607/101
[58] Field of Search ................................ 606/27–34, 41, 606/42; 607/100–102, 154, 156

[56] References Cited

U.S. PATENT DOCUMENTS

| | | |
|---|---|---|
| 4,244,371 | 1/1981 | Farin . |
| 4,416,276 | 11/1983 | Newton et al. . |
| 4,494,539 | 1/1985 | Zenitani et al. . |
| 4,641,649 | 2/1987 | Walinsky et al. . |
| 4,657,015 | 4/1987 | Irnich . |
| 4,841,990 | 6/1989 | Kikuchi et al. .......................... 607/156 |
| 4,924,863 | 5/1990 | Sterzer . |
| 4,945,912 | 8/1990 | Langberg . |
| 5,019,076 | 5/1991 | Yamanashi et al. . |
| 5,045,056 | 9/1991 | Behl . |
| 5,100,388 | 3/1992 | Behl et al. . |
| 5,150,717 | 9/1992 | Rosen et al. . |
| 5,172,699 | 12/1992 | Svenson et al. . |
| 5,188,122 | 2/1993 | Phipps et al. . |
| 5,246,438 | 9/1993 | Langberg . |
| 5,248,312 | 9/1993 | Langberg .................................. 606/28 |
| 5,300,068 | 4/1994 | Rosar et al. .............................. 606/34 |
| 5,300,099 | 4/1994 | Rudie . |
| 5,507,743 | 4/1996 | Edwards et al. .......................... 606/41 |
| 5,628,771 | 5/1997 | Mizukawa et al. ..................... 607/156 |

FOREIGN PATENT DOCUMENTS

| | | |
|---|---|---|
| Wo93/08757 | 5/1993 | WIPO . |
| WO93/20767 | 10/1993 | WIPO . |
| WO93/20768 | 10/1993 | WIPO . |
| WO93/20886 | 10/1993 | WIPO . |
| WO93/20893 | 10/1993 | WIPO . |

OTHER PUBLICATIONS

Langberg, Catheter Ablation of the Atrioventricular Junction Using a Helical Microwave Antenna: A Novel Means of Coupling Energy to the Endocardium, Departments of Medicine, University of California, San Francisco, CA, Dec. 1991, vol. 14, pp. 2105–2113.

Wu et al., "Performance characteristics of a helical microwave interstitial antenna for local hyperthermia," Mar./Apr. 1987, Medical Physics, vol. 14, No. 2.

*Primary Examiner*—Michael Peffley
*Attorney, Agent, or Firm*—Beyer & Weaver, LLP

[57] ABSTRACT

A tunable microwave ablation catheter system is disclosed which matches the impedance of its power supply with the transmission line to minimize reflected power and optimize energy delivery to targeted tissues. The tuner itself may be located in the power supply, the transmission line or the antenna. Tuner mechanisms at these locations can change the antenna configuration, move material relative to the antenna or alter the waveguide. A controller monitors the catheter system operation. A method of medical treatment is disclosed where the impedances of the components of the systems are adjusted during use to compensate for impedance variations.

23 Claims, 12 Drawing Sheets

TUNABLE MICROWAVE ABLATION CATHETER SYSTEM AND METHOD

This is a continuation application of prior application Ser. No. 08/300,948 filed Sep. 6, 1994, now U.S. Pat. No. 5,693,082, the disclosure of which is incorporated herein by reference, which application is a continuation in part of patent application Ser. Nos. 08/062,637 filed May 14, 1993 and 08/163,178 filed Sep. 6, 1994 now U.S. Pat. Nos. 5,364,392 and 5,405,346 respectively, which are incorporated herein by reference in their entirety.

BACKGROUND OF THE INVENTION

The present invention relates generally to ablation catheter systems that use electromagnetic energy in the microwave frequencies to ablate internal bodily materials. More particularly, a variety of tuning arrangements are disclosed for impedance matching the power supply and catheter microwave transmission line components in order to minimize reflected power and maximize catheter to tissue coupling.

Catheter ablation has recently become an important therapy for certain cardiac arrhythmias. Radio frequency (RF) energy is presently accepted as the preferred ablating energy source. Accordingly, a variety of RF catheters and power supplies are currently available to electrophysiologists. Radio frequency energy has several limitations including the rapid dissipation of energy in surface tissues resulting in shallow "burns" and failure to access deeper arrhythmic tissues. Another limitation is the risk of clot formation on the energy emitting electrodes. Such clots have an associated danger of causing potentially lethal strokes in the event that a clot is dislodged from the catheter. A second common ablation approach is the use of high voltage, direct current defibrillator discharges. Direct current ablation has several drawbacks including the need for general anesthesia and explosive discharges that can cause debris or even rupture certain cardiac organs. For these and other reasons, significant attention has been given recently to alternative ablative energy sources.

Microwave frequency energy has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been an interest in using microwave energy as an ablation energy source. The advantage of microwave energy is that it is much easier to control and safer than direct current applications and it is capable of generating substantially larger lesions than RF catheters, which greatly simplifies the actual ablation procedures.

In U.S. Pat. No. 4,641,649, Walinsky et al. disclose a medical procedure for the treatment of tachycardia and cardiac disrhythmia which uses microwave frequency electromagnetic energy to ablate selected cardiac tissue. The microwave energy is transmitted over a coaxial transmission line having an antenna at its distal end. A similar procedure is disclosed in the article by Langberg et al. entitled "Catheter Ablation of the Atrioventricular Junction Using a Helical Microwave Antenna: A Novel Means of Coupling Energy to the Endocardium," PACE, pp. 2105–2113 Vol. 14 (1991). As suggested in the title, the Langberg et al. article proposes the use of a helical microwave antenna at the distal end of the catheter in order to improve the catheter's power delivery characteristics. In U.S. Pat. Nos. 4,945,912, and 5,246,438, Langberg details particular helical antenna designs to be used for cardiac tissue ablation. In the later patent, Langberg recognizes the importance of adjusting the catheter impedance for particular ablation conditions. However, he proposes setting a particular presumed optimal impedance during fabrication. However, this design is not real-time tunable to compensate for the time variation of the impedance over the course of an ablation procedure.

SUMMARY OF THE INVENTION

Accordingly, it is an object of the present invention to provide a tuner for a microwave ablation catheter system that matches the impedance of the power supply and catheter microwave transmission line components in order to minimize reflected power and to optimize the efficiency of the delivery of energy from the power supply to the targeted tissues.

To achieve the foregoing and other objects and in accordance with the purpose of the present invention, a tuner system for a microwave power supply used in an ablation catheter system is disclosed. The tuner system includes a tuner arranged to facilitate matching the impedance of a power generator side portion of the catheter system with the impedance of a catheter side portion of the catheter system. The tuner itself may be located in a variety of positions including in the power supply, on the catheter's transmission line or in the vicinity of the antenna. Several novel tuning arrangements are described. The impedance tuning may be accomplished in a variety of manners including altering the electromechanical configuration of the antenna; moving a material relative to the antenna or vice versa in order to vary the effective impedance during use; and providing a tuning mechanism on the waveguide. In another disclosed embodiment, the impedance matching is accomplished by a tuner mounted in the power supply.

In one embodiment, a reflected power monitor is provided for monitoring the amount of power that is reflected from the catheter during use. The tuning system may also include a tuner controller that receives a signal indicative of the magnitude of the reflected power from the reflected power monitor and generates a control signal based at least in part on the magnitude of the reflected power to automatically match the impedance of the power supply side portion of the catheter system with the catheter side portion of the catheter system.

In a method aspect of the invention, a method for medical treatment using a microwave ablation catheter system is disclosed. The method includes the steps of introducing a catheter having a waveguide and an antenna coupled to the distal end of the waveguide into a patient's body such that the antenna is positioned adjacent material to be ablated. The initial impedance of a catheter side portion of the ablation catheter system is then adjusted to balance the initial impedance of a power supply portion of the ablation catheter system. Microwave energy is applied to the waveguide using a microwave power source coupled to the catheter for a period of time to ablate material in the vicinity of the antenna. The relative impedance of the catheter side portion of the ablation catheter system and the power supply portion of the ablation catheter system are then adjusted during use in order to compensate for impedance variations that occur during use of the catheter.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE INVENTION

A concern in the management of microwave energy is impedance matching of the various transmission line components. An impedance mismatch will reflect some portion of the incident power resulting in reduced energy transmission and increased losses, which is typically manifested as heat generation due to transmission line or wave guide attenuation. With microwave energy ablation, as with radio frequency ablation, the points of greatest impedance mismatch are located at the tip of the catheter. Further, the impedance on the catheter side of the device (as distinguished from the power supply or energy source) tends to vary a fair amount as the catheter is moved about during use and as tissue properties change during an ablation procedure. For example, the impedance of the catheter to tissue coupling will vary with the location at which the catheter tip is placed in the heart. It will also vary during the course of a typical ablation procedure due to changes in the tissue properties as the target tissue is ablated and heating of the transmission line components. When the impedance changes, an increased percentage of the power is reflected and the catheter's performance is reduced.

In coronary applications, the catheter diameter is limited to approximately 7½ French (approximately 2.5 mm in diameter). One problem that arises when using the very small diameter wave guides that are necessitated by such diameter limitations is that the attenuation is quite large over the length of the wave guide. By way of example, in a representative application wherein the transmission line is approximately one meter long and is a coaxial transmission line having a diameter of 72 thousandths of an inch (1.8 mm), the power output of a well tuned system may only be in the range of 25–30% of the input power. Of course, the power output is likely to improve as the technology develops, but attenuation is always likely to be a significant concern.

Figure 1:
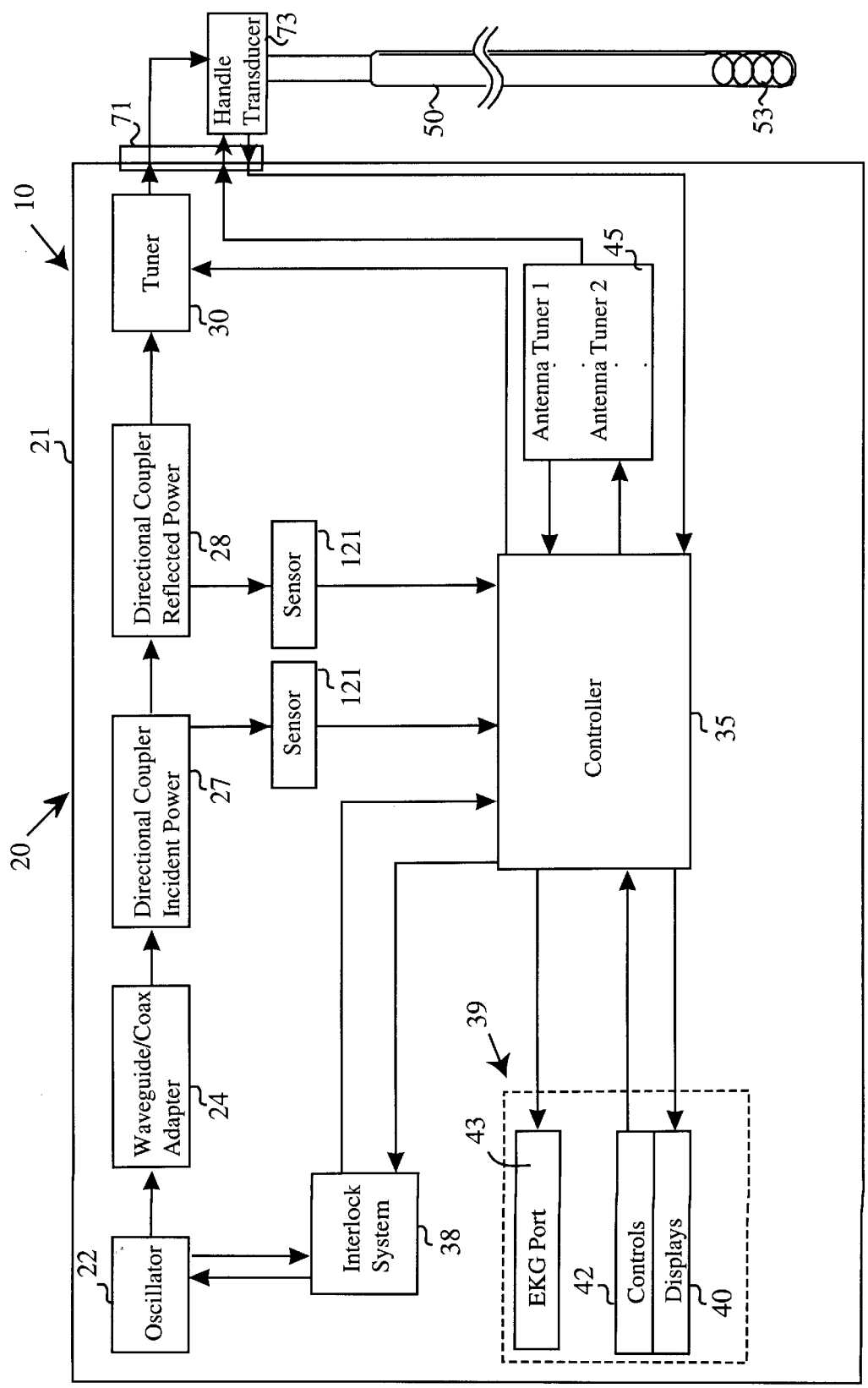
FIG. 1 is a schematic block diagram of a microwave power supply system for an ablation catheter in accordance with one embodiment of the present invention.

In view of the foregoing problems, a variety of microwave catheter tuning arrangements have been developed. Several presently preferred ablation catheter systems in accordance with the present invention will be described below making reference to the accompanying drawings. As seen in FIG. 1, an ablation catheter system 10 generally includes a power supply 20 which is designed to generate controlled microwave energy, a catheter 50 which is designed for insertion into a vessel (such as a coronary vessel) in the body of a patient and a connector 71 for coupling the power supply 20 to the catheter 50.

In the embodiment shown, the power supply 20 includes a casing 21 having a microwave generator 22, a waveguide adapter 24, a pair of directional couples 27 & 28 that interface with power monitors 121, a tuner 30, a controller 35 and an interlock system 38 all enclosed therein. The front panel 39 of the casing has various displays 40 and controls 42, as well as a port 43 to which conventional EKG equipment can be coupled. In one embodiment, a tuning mechanism in the catheter itself may be controlled by antenna tuner 45. The tuner 45 is directed by controller 35.

The microwave generator 22 may take any conventional form. When using microwave energy for tissue ablation, the optimal frequencies are generally in the neighborhood of the optimal frequency for heating water. By way of example, frequencies in the range of approximately 800 MHz to 3 GHz work well. At the time of this writing, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz was chosen. At the time of this writing, solid state microwave generators in the 1–3 GHz range are very expensive. Therefore, a conventional magnetron of the type commonly used in microwave ovens was chosen as the generator. It should be appreciated, however, that any other suitable microwave power source could be substituted in its place.

The microwave energy is transmitted from the microwave generator 22 through a waveguide and coax adapter 24 to a pair of directional couplers 27, 28 used to monitor forward and reflected power respectively. The output of each directional coupler is connected to an associated power sensor 121 which output signals indicative of the forward and reflected power to the controller. It is contemplated that other suitable power monitors could be used in place of the described directional coupler/power sensor arrangements. Following the directional couplers, the transmission line may be equipped with a stub tuner mechanism 30 that is controlled by the controller 35. In several of the described embodiments, a tuning mechanism is provided in the catheter. When such catheters are used, the power supply tuner 30 may be eliminated (although the ability to tune both in the catheter and in the power supply may be advantageous in certain applications). Downstream from the tuner 30, the power is directed through a quick disconnect jack and plug (connector 71) to the catheter 50 itself. The catheter is equipped with an active tuning mechanism, as discussed above. These mechanisms are controlled either manually or automatically by the antenna tuner 45. System controls are provided for operation of the power supply as is a display for such information as system set points, forward and reflected power, temperatures, etc. The controller 35 may take the form of dedicated logic, but in a preferred embodiment a conventional microprocessor or computer is used.

Figure 2:
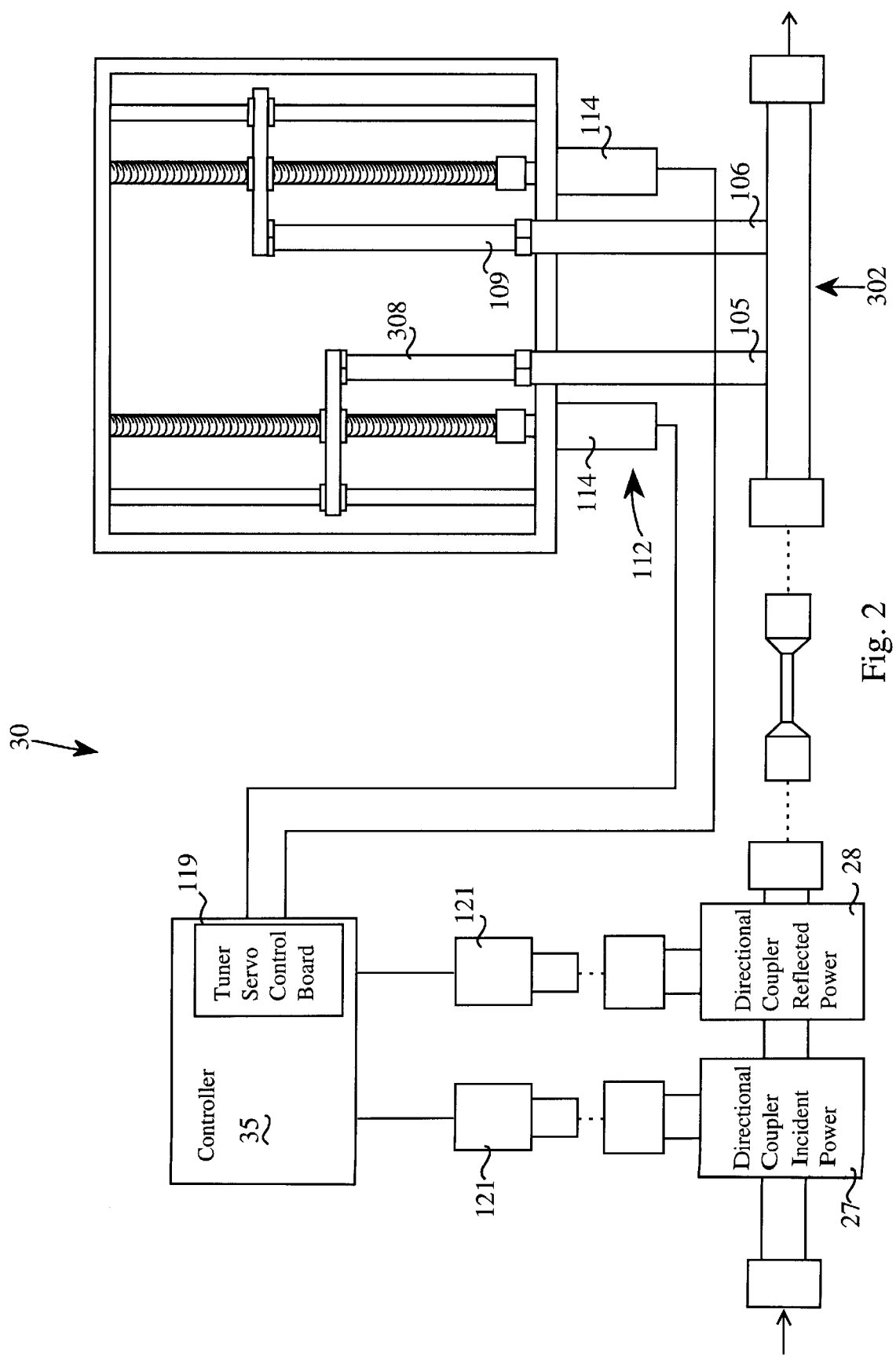
FIG. 2 is a schematic diagram of an automatic tuner system suitable for use in the ablation catheter power supply system shown in FIG. 1.
Figure 3:
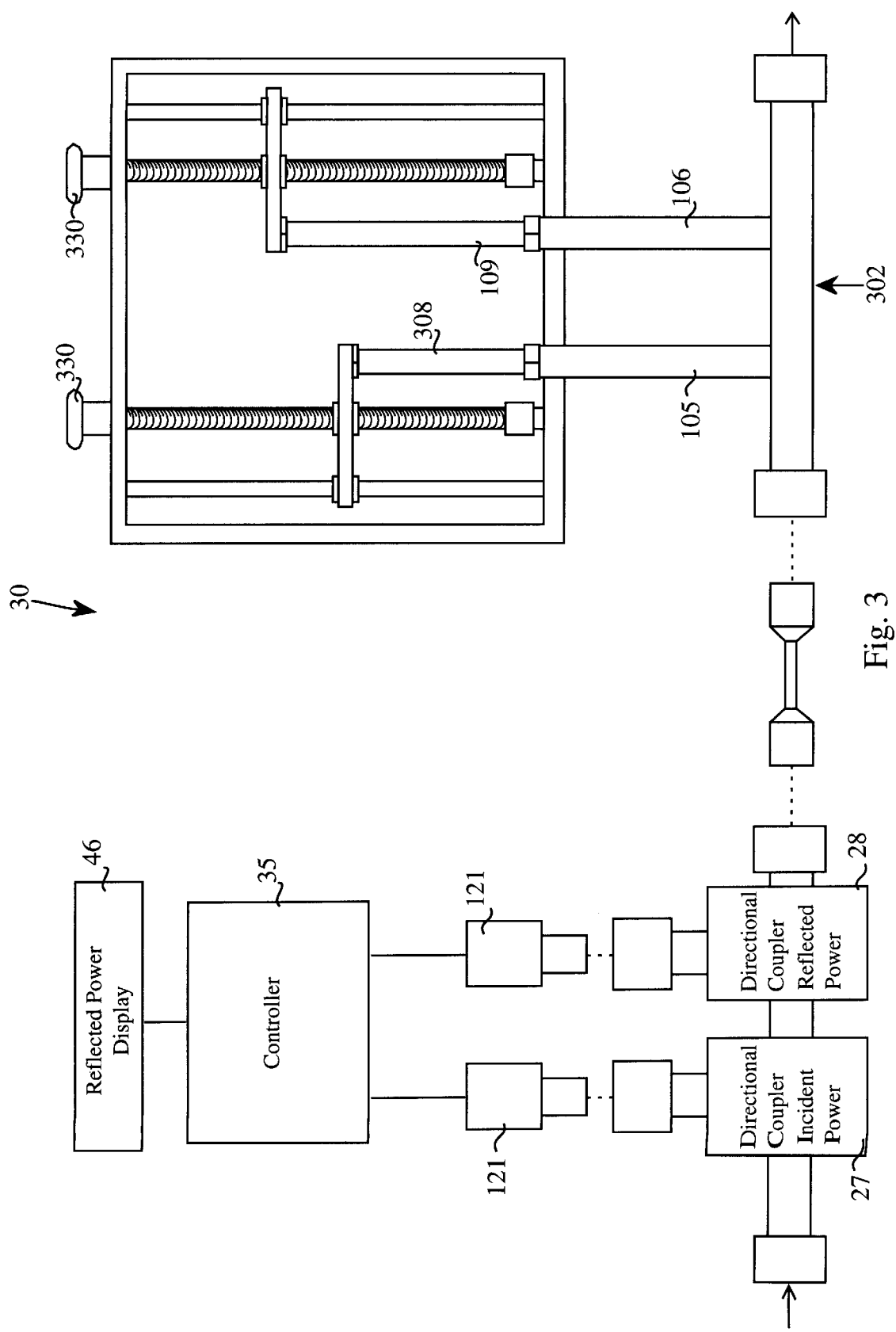
FIG. 3 is a schematic diagram of a manual tuner system suitable for use in the ablation catheter power supply system shown in FIG. 1.

In a typical microwave ablation catheter system, the system is designed to provide a set impedance. Although the actual set impedance may vary, a typical design impedance on the catheter side of the catheter system may be on the order of 50 ohms. However, the impedance tends to vary a fair amount as the catheter is moved about during use and as tissue properties change during ablation. This is true when helical antennas are used. The impedance variations have a number of sources, however a few of the items which have the greatest effect on impedance variations include the catheter tip location, patient to patient tissue variations, and temperature dependent dielectric properties of catheter components and patient tissues. When the impedance changes, the catheter's performance tends to be well below the optimal performance. The decline in performance is most easily seen in the increase in the reflected power. The tuner 30 is therefore provided to compensate for impedance variations that are seen by the power supply during use. In effect, the tuner manipulates the impedance of the catheter side of the catheter system. In the preferred embodiment shown in FIG. 2, the tuner 30 is a conventional stub tuner that has drive units that are arranged to move its stubs back and forth. In an alternative embodiment, the stubs may be manually adjusted by the user either directly (as seen in FIG. 3) or through manual control of the servos 119 (as seen in FIG. 2).

It should be appreciated that the tuner may take the form of mechanically adjustable waveguides or coaxial transmission line arrangements or they may be constructed of discrete component elements connected to the center conductor and outer shield of a coaxial transmission line. In the described embodiment, a coaxial transmission line mechanical tuner commonly referred to as a double stub tuner is used. By way of example, alternative embodiments may utilize a single stub tuner, a triple stub tuner, or a stub stretcher. Any of these tuners may be used in conjunction with a line stretcher to adjust the location of the tuner relative to the sources of the reflected power for further improving the impedance matching capability of the system.

In alternative embodiments, the tuner may be incorporated into the antenna itself in the form of a mechanically adjustable antenna. By way of example, the helical antenna described below with reference to FIG. 8 could readily be arranged in this manner. Alternatively, a balloon mechanism, an expandable basket or other mechanical arrangements could be provided to compress the antenna in a spring like fashion.

The controller 35 may take the form of dedicated logic, but in a preferred embodiment a conventional microprocessor or computer is used. The controller receives inputs from the sensors 121 coupled to directional couplers 27 and 28, the catheter thermometry element 65 (shown in FIG. 6), the interlock system 38 and the controls 42. If desired, the controller can also receive inputs from various other electrodes provided on the catheter and other controls. In FIG. 1 the controller and interlock system are shown as two separate blocks. Although in a discrete logic system, they would typically include separate circuits, when a microprocessor is used as the controller, it can control the interlock system as well.

In all of the embodiments below, the controller operates in accordance with a control algorithm structured to minimize reflected power with respect to forward power and set point power. The control algorithm also provides feedback indicative of the system's operation and allows for identification of potentially dangerous fault and alarm conditions.

The interlock system 38 is intended to shut off the power supply any time it detects the occurrence of a potential problem. In the described embodiment, the interlock system detects: 1) an open casing for the power supply; 2) over heating of the microwave generator (this is unlikely to be a problem when the magnetron in the first described embodiment is used. The generator overheating interlock is more important in solid state systems); 3) overheating of the tissue or catheter elements; 4) when the catheter is damaged for any reason; and 5) when the catheter is not plugged into the power supply. Of course, the interlock system could be activated by a variety of other events as well.

By way of example, the open casing may be detected by a switch that is closed when the casing cover is secured. Overheating of the microwave generator may be detected by thermometry elements attached to the generator housing. Overheating of tissues or catheter elements is detected by thermometry element 65 (shown in FIG. 6). Damage to the catheter may be detected as exceeding reflected vs. forward power boundary conditions or limits, sudden changes in reflected power or open circuit electrode, transmission line, or thermometry element conditions in the event of catastrophic damage.

The controller can also be programmed to test for sudden changes in a variety of signals in search of faults which warrant shutting down of the microwave generator. By way of example, sudden changes in the reflected power are often a sign of a dangerous conditions as catheter damage, coagulation, or excessive tissue damage. Tests for shorts or open circuits will indicate catastrophic catheter damage. Thus the controller 35 may be used as an integral part of the interlock system.

Referring next to FIG. 2, a first embodiment of the tuner 30 will be described in more detail. In this embodiment of the tuner, an automatic feedback control is provided to minimize reflected power. A double stub tuner 302 is coupled on each end to coaxial cables which serve as the microwave waveguides. The stub tuner has a pair of stub arms 105, 106 which slidably receive plungers 308, 109 therein. A pair of motorized drive units 112 are provided with each drive unit 112 being associated with one of the plunger arms. Each drive unit 112 includes a motor 114, which can be controlled by controller 35. The controller 35 is arranged to receive a signal indicative of the magnitude of the reflected power from directional coupler 28. The controller will then adjust the tuning mechanism accordingly via a servo or stepper motor controller (119).

Referring next to FIG. 3, a manually adjusted version of the tuning system will be described. In this embodiment, a pair of adjustment knobs 330 are provided which allow the user to manually manipulate the plungers 308, 109. The adjustment knobs 330 are mounted on the front display panel 39. In this case, the power sensor 121 again feeds the controller 35 which in turn provides a display signal to the reflected power display 46. The user can thus visually monitor variations in the reflected power and make suitable adjustments in the settings of the plungers of the stub tuner, thereby controlling the effective impedance of the catheter side of the ablation catheter system.

A hydraulic or pneumatic control linkage between the antenna tuner(s) 45 and the catheter 50 of FIG. 1 is provided with a quick disconnect interface 71. The convenience of such a quick disconnect should be apparent. The linkage can be transduced in the catheter handle 73 into other energy transmitting alternatives such as torsional wire actuation, axial wire actuation, or electrical actuation as required for any particular application.

Figure 4:
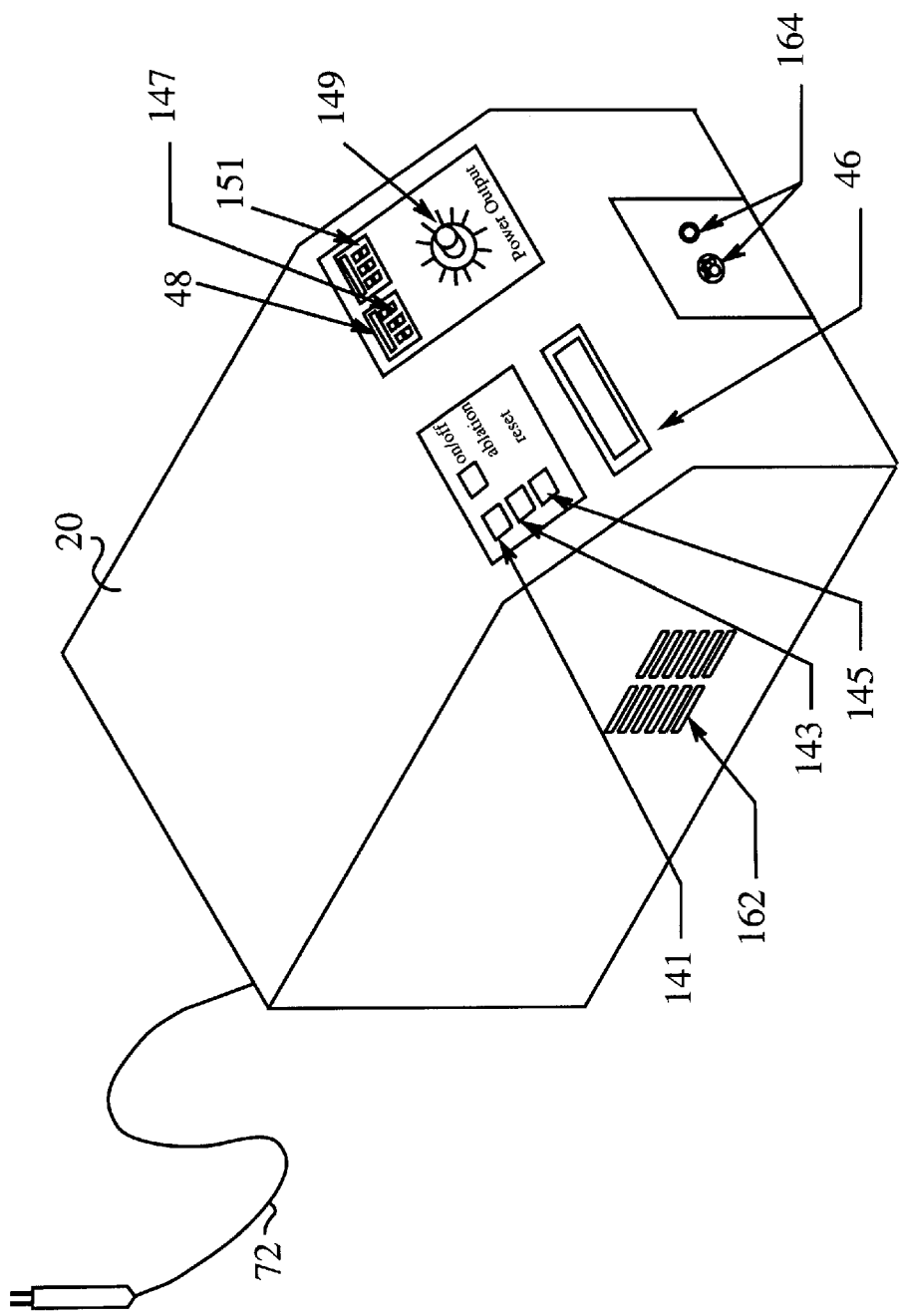
FIG. 4 is a schematic diagram of a display panel suitable for use in the ablation catheter power supply system shown in FIG. 1.

Referring next to FIG. 4, a representative display panel will be described. As seen therein, the display panel may include any number of suitable knobs and dials as for example, an on/off switch 141, an ablation start switch 143, a reset switch 145, a timer 147, and a power control dial 149. It may also include any number of suitable displays including by way of example, a reflected power display 46, a time display 48 and thermometry displays 151. In embodiments having a manually adjusted tuner, the adjustment knobs 330 may be provided as well. The power supply may also include air vents 162 for cooling and connectors 164 for coupling with the catheter and external electronics.

The power control switch 149 and timer control 147 permit the user (doctor) to control the power output. By way of example, in one described embodiment, the power control switch 149 permits the outputting of between 20 and 65 watts. The timer control switch 147 is provided to allow the user to control the length of the ablation procedure. Typical use times are up to approximately 100 seconds. Of course, this number may vary widely in accordance with the needs of a particular system.

The reflected power display 46 is another safety feature. If something happens to the catheter during use, the reflected power will increase dramatically. Thus, the reflected power display gives the doctor additional feedback which may indicate that a problem exists.

Figure 5:
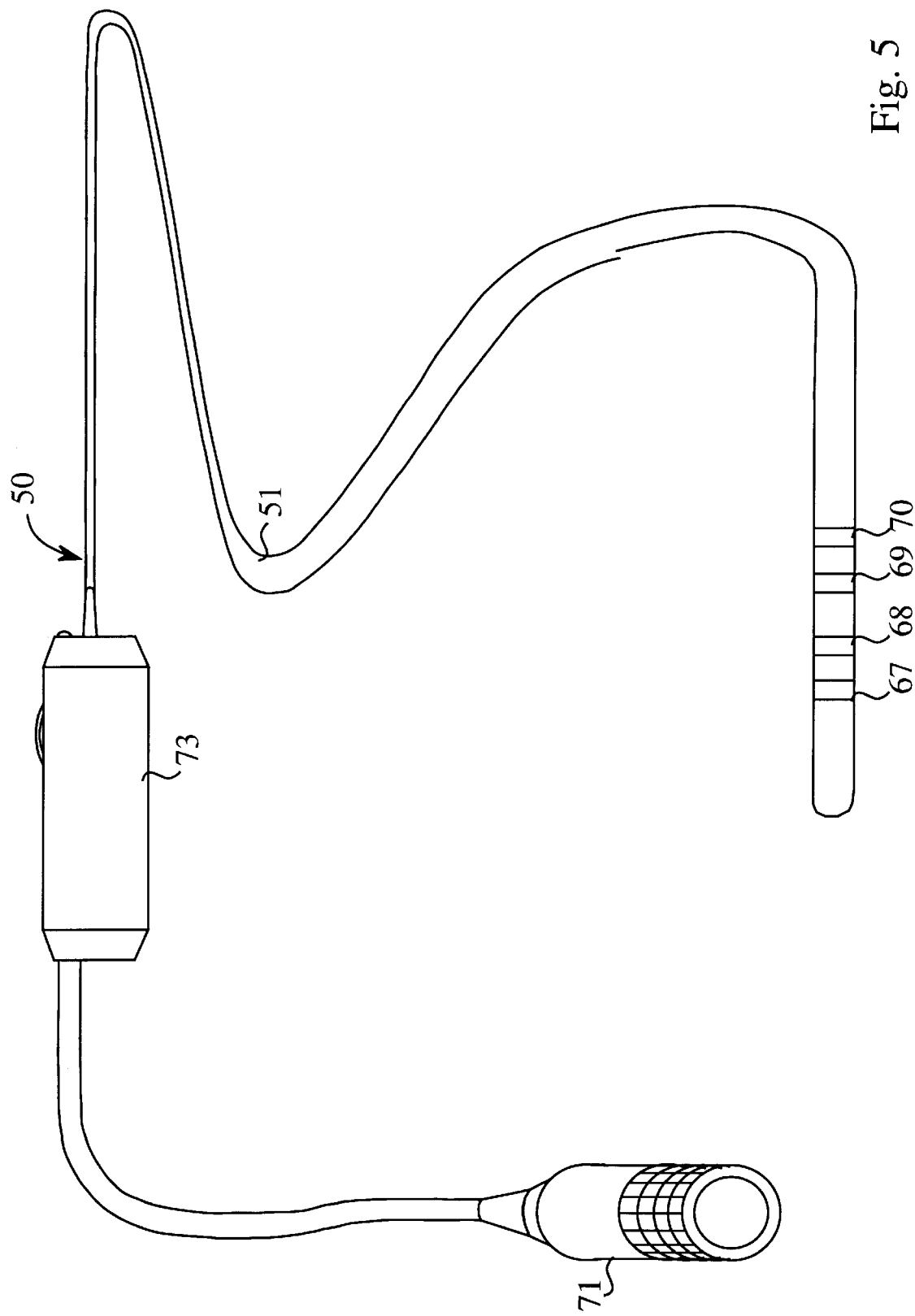
FIG. 5 is a diagrammatic view of an ablation catheter formed in accordance with the present invention.
Figure 6:
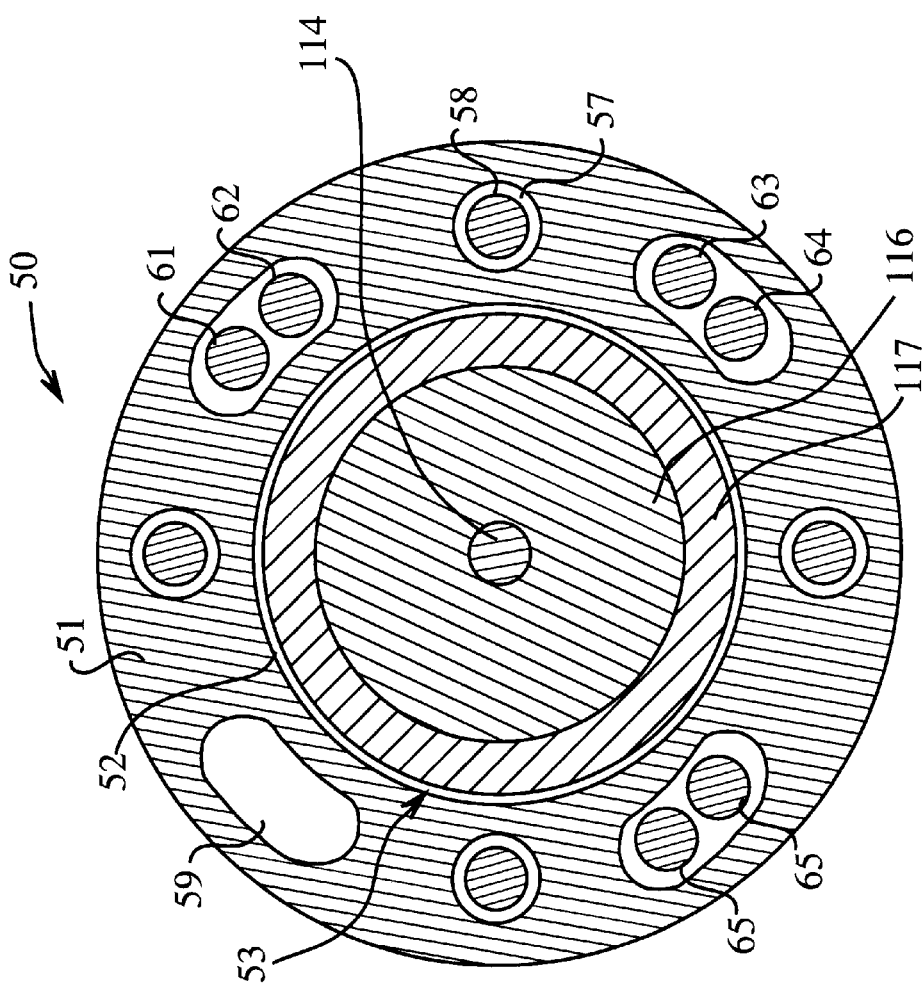
FIG. 6 is a diagrammatic cross sectional view of a tubular member in accordance with the present invention along an uninterrupted portion of the catheter.
Figure 7:
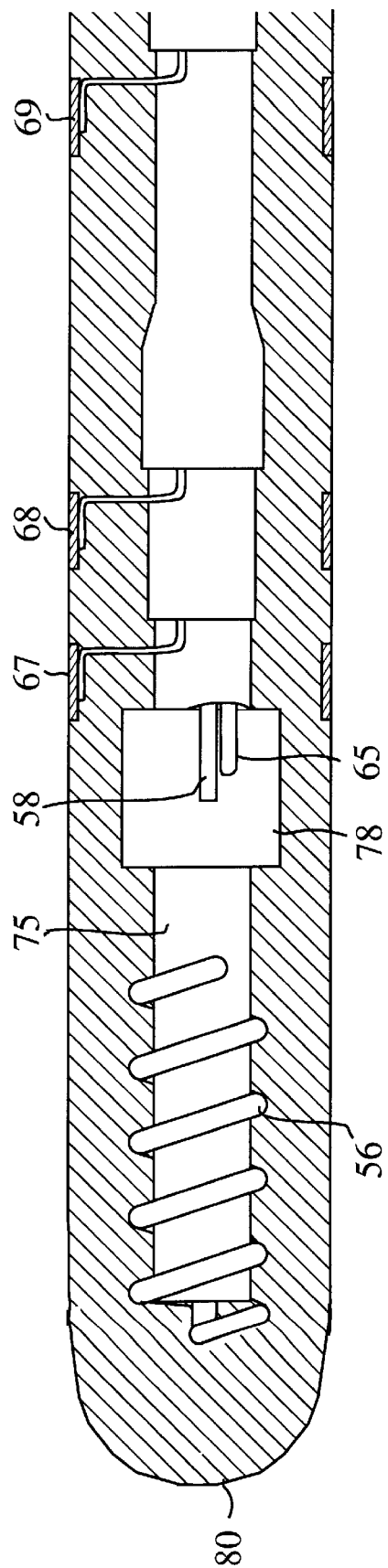
FIG. 7 is a enlarged diagrammatic side view of the tip portion of one embodiment of an ablation catheter in accordance with the present invention.

Referring to FIGS. 5, 6 and 7 a suitable catheter construction for use in a system that incorporates a power supply based tuner will be described. The catheter 50 includes outer tubing 51, a coaxial microwave transmission line 53, a helical antenna 56, stiffener wires 58, a plurality of electrode wires 61–64, thermometry elements 65, steering elements and electrodes 67 and a connector 71. The outer tubing 51 may be made of any suitable material such as medical grade polyolefins, fluoropolymers, or polyvinylidene fluoride. Further, PEBAX resins from Autochem of Germany have been used with success for the outer tubing of the body of the catheter. However, Teflon type products are preferred for the tip. The connector 71 couples the transmission line 53 to the external power supply 20.

A series of electrodes 67–70 may be provided near the tip of the catheter to monitor the patient's condition and/or the nature of the ablation process. In the described embodiment, the information obtained from the electrodes 67–70 is transmitted through the power supply to external electronics. Filtering of the signal may be provided as necessary. In alternative embodiments, some of the external electronics could be incorporated into the power supply and/or the power supply could use information obtained from the electrodes in its control scheme.

As seen in FIG. 6, the tubular member 51 has an enlarged central lumen 52, a plurality of stiffener lumens 57 and a plurality of elongated component lumens 59. The central lumen 52 is sized to receive the coaxial transmission line 53. The stiffener lumens 57 receive stiffener wires 58. The other various wires (such as the electrode and thermometry wires) may be run through the component lumens 59. Alternatively, in embodiments that utilize one or more inflatable balloons, either the stiffener lumens 57 or the component lumens 59 may be used to pass a fluid suitable for inflating the balloon(s).

The current thinking is that in order to transmit microwave energy in small diameter environments, the wave guide should be a coaxial cable. Therefore, a coaxial wave guide is selected that is suitable for transmitting microwave energy. A suitable wave guide is the AS450–3050 coaxial cable supplied by Cooner of Chatsworth (Calif.). Of course, the diameter of the coaxial transmission line 53 will vary depending upon the needs of a particular system. However, generally, the larger the diameter, the better the microwave transmission characteristics will be. By way of example, as indicated above, in coronary applications, the catheter diameter is typically limited to approximately 7½ French (approximately 2.5 mm in diameter). In such a system, a wave guide that is approximately one meter long and has a diameter of 72 thousandths of an inch (1.8 mm) works well. The stiffener wires 58 may also represent a mechanical flexure device allowing for flexure control and improved steering. The thermometry elements 65 may take the form of thermocouple wires, fiber optic sensor cables or any other suitable thermometry devices.

A catheter tip without a tuning mechanism is shown in FIG. 7. A series of four electrodes 67–70 are provided at the tip of the catheter. The electrodes are provided for monitoring the patient's condition and/or the nature of the ablation process. In the described embodiment, the information obtained from the electrodes 67–70 is not used for the power supply, but rather is supplied to external electronics via connector 72 which is shown in FIG. 4. In alternative embodiments, some of the external electronics could be incorporated into the power supply and/or the power supply could use information obtained from the electrodes in its control scheme.

A shield 78 is positioned behind the antenna with the various electrodes and metallic wires being located behind the shield. Thus, the shield serves as an electromagnetic shield for the electronics. The distal end of the thermometry element 65 are positioned back from the distal edge of a shield 78. The electrodes 67–70 (electrode 70 is not shown) are positioned proximally relative to the antenna. Similarly, the distal end of stiffening wire 58 is positioned proximally relative to the shield. The reason for the positioning of the thermocouple, the electrodes and the stiffening wire behind the shield is to prevent their interference with the electromagnetic field and vice versa.

As seen in FIG. 7, a dielectric support 75 is coupled to the distal end of the coaxial transmission line 53 in the vicinity of the antenna 56. In the embodiment shown, the dielectric support has the helical antenna 56 wrapped thereabout. Since the field produced by the antenna is very intense on the coil's interior, it is important that the dielectric support material be capable of withstanding intense electromagnetic fields in the microwave frequency range. By way of example, a suitable dielectric material is Teflon, although other suitable materials could be used as well.

Although the geometry of the antenna 56 may vary in accordance with the needs of a particular application, a helical coil type antenna having a total length (i.e. length of the wire along the coil as opposed to the longitudinal length of the coil) equal to either one eighth or one quarter of the wavelength of the transmitted microwave energy (or a multiple thereof) has been found to work particularly well when the goal is to develop a strong field to the side of the antenna, which is desirable for certain applications. This antenna configuration also exhibits particularly good coupling to the transmission line. In view of this characteristic, the optimal actual length of such an antenna will vary in accordance with the selected frequency. The characteristics of the helical coil type antenna are the result of a variety of characteristics including shield (ground plane) to antenna gap, coil pitch, wire size, wire geometry and coil diameter.

It should be appreciated that the actual antenna geometry can be varied widely in accordance with the type of ablation that is desired for a particular application. For example, the helical antenna shown is particularly good at developing a strong electromagnetic field to the side of the catheter tip. On the other hand, a straight antenna tip that extends slightly beyond a shield may be more effective at developing fields that extend from the distal end of the catheter.

The tip of the catheter in the region of the antenna is insulated with a suitable insulation material 80 such as silicone or Teflon. By insulating the antenna 56, the described catheter avoids the charring and tissue destructing effects that are commonly experienced with exposed (uninsulated) catheter tips. Regardless of the type of microwave antenna used, the dangers of current induced charring caused by an uninsulated antenna may be overcome by insulating the antenna tip with a suitable dielectric material that is capable of withstanding the high energy field produced during use. Such insulation will eliminate all adverse current affects and will cause the abating process to be carried out solely on the basis of the electromagnetic fields that are generated. It is believed by the inventors that this insulating feature will become very important as the development of microwave catheters progresses. By eliminating the risks of charring, the risks of debris generation are virtually eliminated, temperature is controlled, and penetration is increased.

Due to the inherent inefficiencies of electrically small antennas and the potential of unavoidable reflections from the junction between the coaxial transmission line and the antenna assembly, it is desirable to tune the system with a tuning mechanism in close proximity to the source of the reflected power, ideally at an appropriate location that is a distance of less than one wavelength from the antenna junction. Several presently preferred embodiments capable of providing catheter based tuning will be described below.

A wide variety of factors will affect the impedance of the antenna. In addition to the external factors previously discussed, the antenna's geometry will have a strong influence on the overall impedance. Some of the factors include the coil diameter, the pitch, the length of wire used, the gap, the wire diameter and cross sectional shape, and the dielectric properties of surrounding mediums. The spacing of the turns of the coil is determined by their pitch or the lead angle. Of course, the spacing between turns does not need to be constant over the length of the coil. The spacing between the first turn of the antenna coil and the distal face of a shield termination is referred to as the gap. Other catheter factors that influence the antenna's impedance include the composition, mass, location and electrical properties of the other components within the catheter tip. Optimization of the energy coupling between the transmission line and the targeted tissues requires careful selection of the parameters discussed above, each of which can be considered as a variable that may be used to adjust the impedance and energy transmission characteristics of the antenna.

Figure 8:
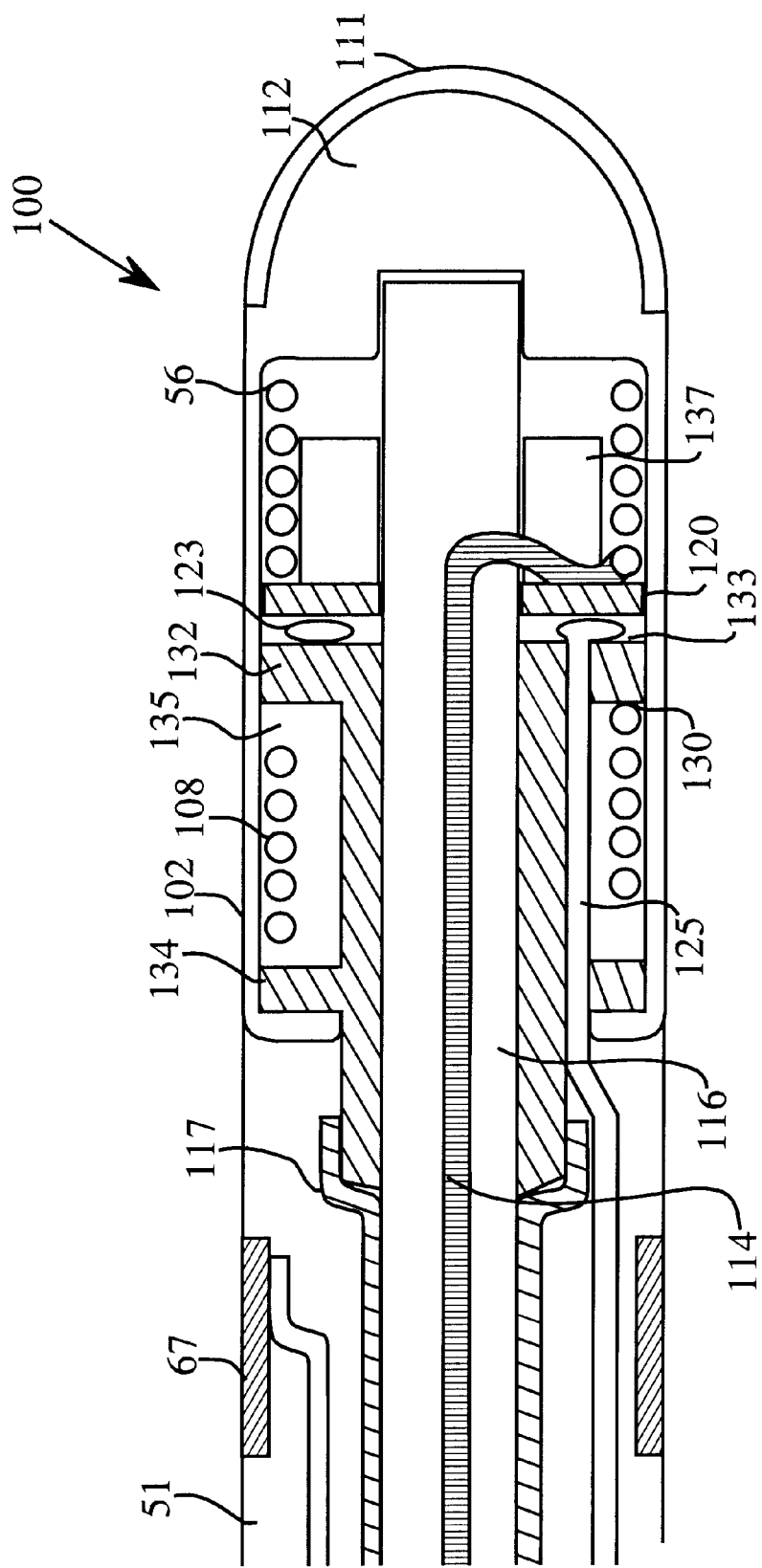
FIG. 8 is a diagrammatic cross sectional side view of the tip portion of another embodiment of an ablation catheter in accordance with the present invention.

Referring next to FIG. 8, a presently preferred embodiment of the invention that includes a tunable antenna will be described. The catheter tip 100 is encased within a insulating shell 102 formed from a dielectric material such as silicone or Teflon. The shell 102 insulates the antenna 56 to avoid the charring and tissue destruction effects that are commonly experienced with exposed (uninsulated) catheter tips. The shell 102 encloses a pair of helical coils which include an antenna coil 56 and a ground coil 108. An electrode 111 is provided at the distal end of the shell and is supported by an enlarged dielectric plug 112 that is formed integrally with the shell 102. The antenna coil 56 is coupled directly to the center conductor 114 of the coaxial transmission line 53 to make a smooth transition between the transmission line and the helical antenna coil 56.

In the embodiment shown, the connection is made at the proximal end of the antenna. However, it should be appreciated that the connection may be made at any point along the length of the coil. It should be appreciated that movement of the connection point is expected to have an impact on the electromagnetic field generated by the antenna and upon the impedance characteristics of the antenna. The antenna coil 56 may be formed from a variety of materials that exhibit good conducting and flexibility properties. By way of example, silver-plated stainless steel spring wire is an excellent material for this application.

The dielectric support portion 116 of the coaxial transmission line extends beyond the point where the center conductor is attached to the antenna coil 56 so that it extends co-axially through the entire antenna coil and into a supporting recess in the dielectric plug 112. The dielectric support 116 also serves as a guide for slider 137. Since the field produced by the antenna is very intense on the coil's interior, it is important that the dielectric support material be capable of withstanding intense electromagnetic fields in the microwave frequency range. By way of example, a suitable dielectric material is Teflon, although other suitable materials or mediums could be used as well.

A shield termination 130 is coupled to the shield portion 117 of the coaxial transmission line 53. The shield termination 130 has an enlarged head 132 at its distal surface. Various electrodes and metallic wires are located proximal of the shield termination head for protection from the strong electromagnetic fields generated during use. Thus, the shield termination serves as an electromagnetic shield for the electronics. The shield termination 130 extends proximally beyond the dielectric shell 102 to make a good connection with the shield 117 which anchors the catheter transmission line. The connection can be made using any suitable connection technique such as soldering, brazing or crimping. The shield termination also includes an enlarged anchor portion 134 that mates with the proximal end of the shell to secure the shell in place. The anchor and head portions of the shield termination 130 cooperate to form a bobbin like structure having an opening 135 that receives the ground coil 108. The distal end of the thermometry element 65 (not shown) are positioned behind the head portion 132 of the shield termination. The electrodes 67 are positioned proximally relative to the shell 102. Similarly, the distal end of stiffening/steering wires 58 are positioned proximally relative to the antenna. The reason for the positioning of the thermocouple, the electrodes and wire elements behind the shield is to prevent their interference with the electromagnetic field and vice versa.

To adjust the antenna's impedance, a slidable thrust plate 120 is provided between the proximal end of the antenna coil 56 and the shield termination head 132. The thrust plate 120 is driven by a balloon actuator 123 that is located between the thrust plate and the face 133 of the shield termination. (A suitable system for controlling hydraulic or pneumatic pressure within the balloon was discussed in relation to FIG. 3a.) Thus, the shield termination 130 acts as a surface against which the balloon actuator 123 may push in order to regulate the position of the thrust plate. The balloon actuator 123 is fed by a feed tube 125. A slider 137 is provided distal of the thrust plate and serves to balance the thrust plate 120 so that it moves evenly in an orientation that is substantially perpendicular to the longitudinal axis of the catheter. More specifically, the slider is secured to the thrust plate and is closely journaled around the dielectric support 116 to insure that the thrust plate 120 does not wobble as it translates. Electrical properties of the slide 137 may be selected appropriately based upon the needs of a particular catheter.

In one preferred embodiment, the thrust plate 120 is formed from a conductive material in capacitive proximity with the proximal face 133 of the shield head 132. The balloon actuator 123 is then used to vary the distance between the two surfaces. The resulting capacitance interaction between the shield and the thrust plate follows the well known equation:

$$C = keA/d,$$

where "k" is the dielectric constant, "e" is the permittivity constant, "A" is the area of the opposing surfaces, and "d" is the distance between the surfaces. Thus, by varying the distance between the shield's termination head 132 and the thrust plate 120, the apparent impedance of the catheter side of the ablation system can be readily controlled, which permits good impedance matching. It is noted that with this arrangement, the thrust plate 120 is attached to the slider 137 to assure uniform variation of the distance between the facing surfaces of the thrust plate and the shield 130. Further, the proximal end of the antenna coil 56 is attached to the thrust plate 120 and a small gap may be provided between the distal end of the antenna coil 56 and the dielectric plug 112. Therefore, the antenna coil has room to slide back and forth with the thrust plate 120.

In an alternative embodiment, the thrust plate 120 is formed from a non-conductive material such as Teflon and is used to mechanically adjust the length of the antenna coil 56. It should be appreciated that variations in any of the coil's dimensions, including length, width and pitch will vary the impedance at the catheter tip. Accordingly, the antenna's impedance may be adjusted by varying the length of the antenna coil. In this embodiment, the distal end of the antenna coil preferably abuts against or is coupled to the proximal surface of the dielectric plug 112 so that the plug serves as an anchor point for the coil. At the same time, the proximal end of the antenna coil 56 is secured to the thrust plate 120. Thus, movement of the thrust plate back and forth will cause the compression and extension of the antenna coil.

In yet another embodiment of the invention, the slider 137 may be used as a tuning slug. That is, the impedance seen by the antenna may be adjusted by moving the slider back and forth relative to the antenna coil 56. In this embodiment, the antenna coil 56 is not connected to the thrust plate so that it is independent of movement of the thrust plate. To maintain the independence of movement, the diameter of the thrust plate may be reduced, or a space may be provided between the thrust plate 120 and the antenna coil 56. The slider may be constructed of any suitable dielectric, conductive, or ferrite materials to accomplish the objectives of the invention depending upon the tuning behavior desired for a particular application. For example, when a dielectric material is use as the slider, the higher its dielectric constant, the greater the range of adjustment for a given mechanical translation.

The ground coil 108 is used to further improve the performance of the antenna assembly. The ground coil 108 is attached to the shield termination head 132 in close proximity to the shield termination face 133. Best results are achieved when the ground coil 108 is a mirror image of the antenna coil 56. Therefore, again a wire length equal to a quarter wavelength (or failing that, an eighth wavelength) is preferred. The ground coil 108 functions similarly to the common "bazooka" configuration frequently used in electrically small microwave antennas. However, such "bazooka" configurations would be too cumbersome to use in this application. A properly sized and positioned ground coil tends to help focus the electromagnetic field and therefore increases penetration at a given power setting.

In certain antenna configurations, it may be desirable to coil the wire of the antenna with a pitch that is smaller than that which would be possible with a round wire. By way of example, to achieve circular polarization with an electrically short helical coil antenna, the following formula described by Stutzman and Thiele in their text entitled *Antenna Theory and Design*, John Wiley & Sons (1981), may be used:

$$C = \pi D = (2S(1))^{1/2}$$

For a wavelength of 12.25 cm corresponding to 2.45 GHz in free space and a diametric constraint of 2 mm, the pitch, S, would be about 0.016 mm. If the center conductor of the coaxial transmission line feeding the antenna was 0.025 mm, a pitch of 0.016 would not be possible with a round wire. To account for this and preserve the surface area available for current conduction, a rectangular cross section may be used.

The distal electrode 111 is useful for accurately positioning the catheter during an ablation procedure. The primary challenge to the use of a distal electrode is the electrical accessibility and electrical insulation of the electrode. Any conducting material in the field of the antenna will result in distortion of the electrical field and potential conduction of energy away from the antenna in the direction of the power supply end of the catheter. The distal electrode is electrically isolated from the antenna itself and is accessed with a contact wire. A contact wire guide tube (not shown) is passed through the shield termination face in close radial proximity to the balloon actuator feed tube and occupying the gap between the two ends of the balloon actuator. The tube continues through guide holes in the thrust plate 120 and slider 137, and is terminated in the dielectric plug 112. The guide tube is formed from a suitable dielectric material such as Teflon.

A guide wire may be advanced manually or automatically through the region of the antenna and into contact with a recess in the distal electrode 111. Plated stainless steel spring wire is a preferred material for the guide wire. Alternatively, the guide tube may take the form of a fluidic capillary used to transmit pressure to a switch mechanism providing contact between the antenna itself and the distal electrode whereby the positioning signal is read on the center conductor of the microwave transmission line accessed via a coaxial switch or filter arrangement. This alternative can be configured for rapid cycling of the switch mechanism allowing for automatic and periodic sensing timed with intermittent cycling of the microwave power.

Figure 9:
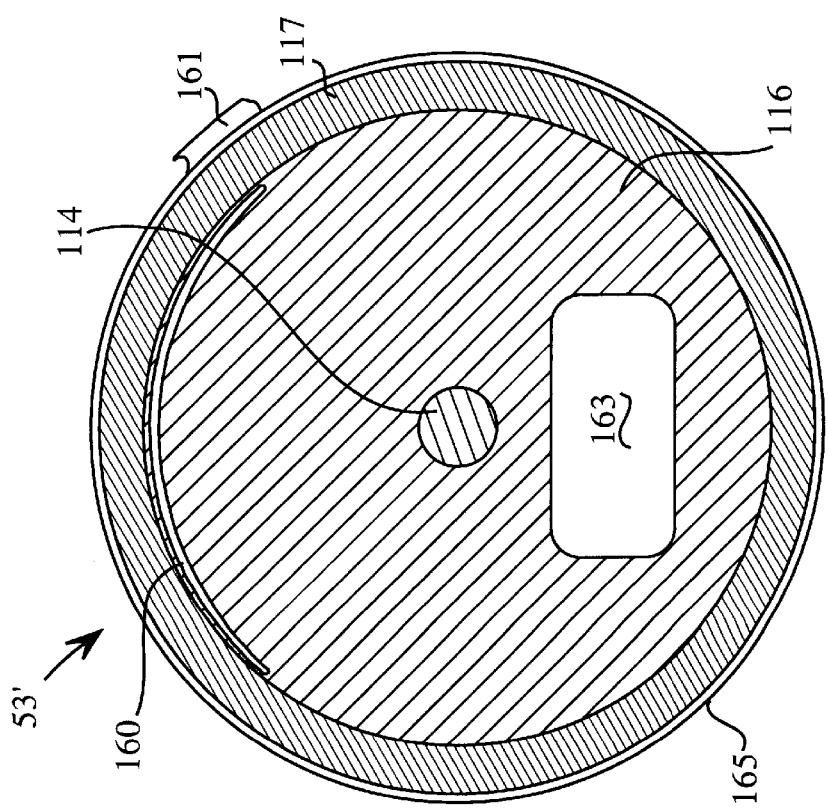
FIG. 9 is a diagrammatic cross sectional view of a coaxial transmission line in accordance with another embodiment of the present invention which includes a tuning balloon that is suitable for altering the cross section of the coaxial transmission line by deflecting the center conductor.

Referring next to FIG. 9, an alternative embodiment of the invention that includes a quarter wavelength tuner that distorts the coaxial transmission line itself to accomplish tuning will be described. In this embodiment, a tuning balloon 160 is inserted into a quarter wavelength long portion of the coaxial transmission line between the shield 117 and the dielectric support 116. The tuning balloon 160 is placed in close proximity to the location of the impedance mismatch. Preferably adjacent to or within one wavelength of the antenna junction. The optimal location for the tuner is a function of the impedance characteristics of the antenna itself. Inflation of the tuning balloon 160 presses against the dielectric support 116 creating a side load on the center conductor 114 which in turn distorts the cross section of the transmission line and changes the impedance of the distorted portion. The tuning balloon is longitudinally tapered to facilitate a smooth transition from the undistorted transmission line to the distorted portion. This provides a smooth variation of the characteristic impedance of the line. By way of example, the tuning balloon may be formed from thin wall polyester tubing that is pinched off and sealed at one end. If room permits, it is desirable to have both ends of the tuning balloon tapered. However, in certain applications it may be necessary to have just one or even neither of the ends tapered. The tuning balloon 160 may be filled through port. It should be appreciated that the transmission line 53' shown in FIGS. 9 and 10 will be received within the central lumen of the catheter's outer tubular member 51.

Figure 10:
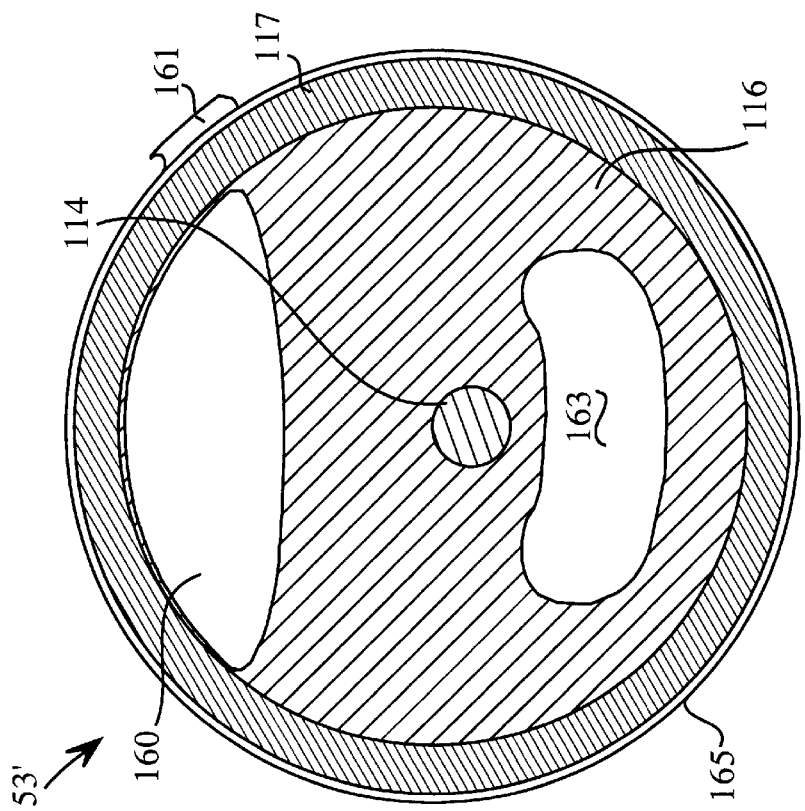
FIG. 10 is a diagrammatic cross sectional view of the transmission line shown in FIG. 9 with the tuning balloon in the inflated position.

A flexure cavity 163 is provided within the dielectric support 116 on the opposite side of the center conductor 114 as the tuning balloon 160. The flexure cavity 163 provides a recess that the center conductor can move towards as the tuning balloon is inflated. Therefore, it serves to minimize distortion of the shield. The lateral motion of the center conductor 114 caused by inflation of the tuning balloon is illustrated in FIG. 10. A shield support 165 serves to protect the integrity of the transmission line shield 117. Thin wall polyester shrink tubing is a suitable material for the shield support. The tuning balloon can be installed from the distal end of the catheter transmission line or from a proximal direction through a hole in the transmission line shield, leakage from which is avoided with an additional grounded sleeve installed in a triaxial fashion. In practice, it is quite difficult to provide a flexure cavity 163. Accordingly, it is preferable to provide an alternative structure that provides the same mechanical effect as the flexure cavity. For example, a foamed or expanded material can be used in the dielectric to absorb the deflection.

The function of the quarter wavelength tuner is to match two structures with differing characteristic impedances. These structures will be matched by a quarter wavelength transmission line when the characteristic impedance of the quarter wavelength transmission line is equal to the geometric means of the impedances of the two mismatched structures. This phenomenon is discussed in Wolff's text *Microwave Engineering and Systems Applications* published in 1988 by John Wiley & Sons. Therefore, for a catheter transmission line with a characteristic impedance of $Z_O$ and an antenna assembly with an equivalent characteristic impedance of $Z_L$. The characteristic impedance, $Z_T$, required for the quarter wavelength tuner is $Z_T=(Z_O Z_L)^{1/2}$. The theoretical value of the transmission line impedance with a shifted center conductor can be calculated using the following formula derived from Transmission Line Design Handbook by Wadell:

$$Z_O = 0.159 \ Q^{-1/2} k \ cosh^{-1}[R(1.0-X^2R^{-2})/2.0r+r/2.0R]$$

where Q is the permittivity constant, k is the dielectric constant, r is the radius of the center conductor, R is the radius of the dielectric material and X is the displacement of the center conductor from the centerline of the transmission line.

Figure 11:
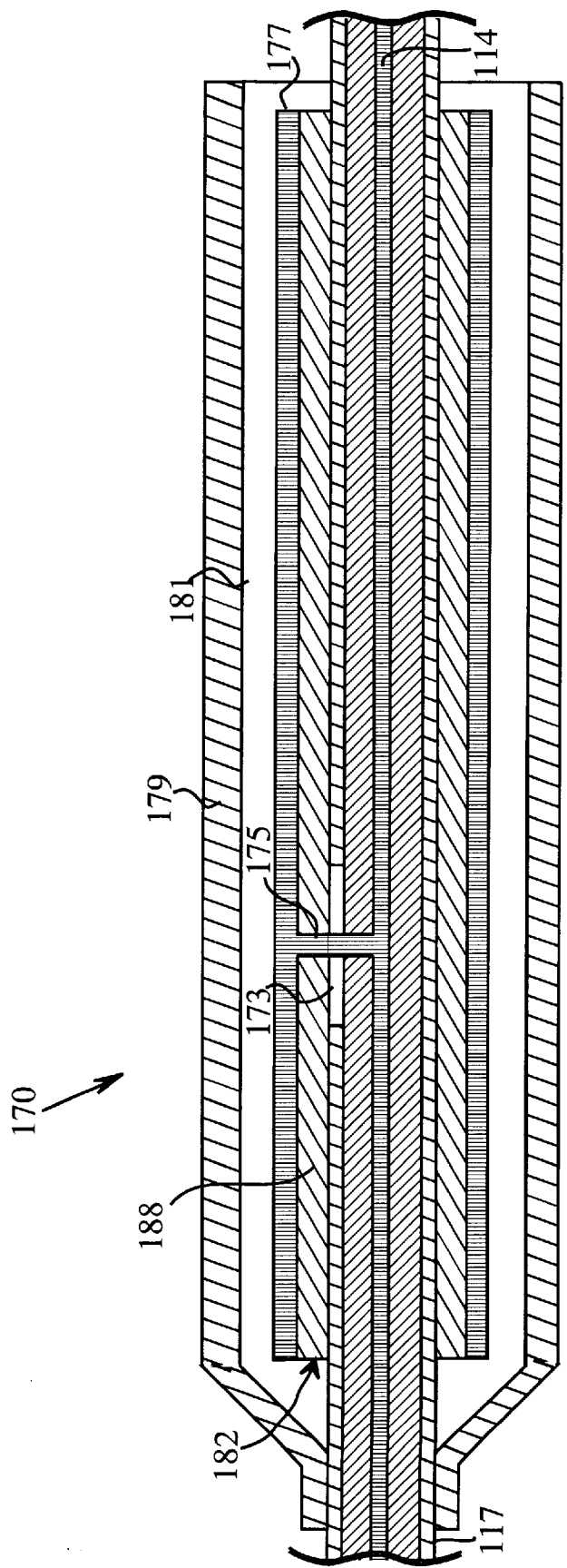
FIG. 11 is a diagrammatic cross sectional side view of a co-axial capacitive tuner connected to the coaxial transmission line in accordance with another embodiment of the invention.

Referring next to FIG. 11, another alternative embodiment of the transmission line that includes a coaxial capacitive tuner 170 will be described. Although the capacitive tuner 170 may be connected to the transmission line 53 at any location along the length of the transmission line, the performance will be the best when the tuner is located in the vicinity of the impedance variations. That is, close to the antenna assembly. Preferably, the tuner will be positioned within one wavelength of the antenna. The coaxial capacitive tuner includes a slot shaped opening 173 formed in the shield of the transmission line. A post 175 extends through the slot 173 and is connected to the center conductor 114. The post 175 supports a tuning sleeve 177 which is capacitively coupled to the transmission line shield 117. A ground plane shield 179 encloses the tuning sleeve 177 to prevent electromagnetic emissions. An inner dielectric cavity 182 is formed between the transmission line shield 117 and the tuning sleeve 177. An outer dielectric cavity 181 is formed between the tuning sleeve 177 and the ground plane shield 179. In some embodiments, highly insulative dielectric materials 188 are placed in one or both of the dielectric cavities.

The capacitance of the tuner is adjusted to achieve the desired tuning. This adjustment may be accomplished in a wide variety of manners. By way of example, a coaxial balloon located in place of the dielectric material 188 may be used to mechanically vary the distance between the opposing capacitive plates. Alternatively, a coaxial dielectric slug may be moved axially in a capacitor dielectric cavity to effect the desired tuning. The slug may be positioned in either the outer dielectric cavity 181 or the inner dielectric cavity 182. It should be appreciated that a variety of other mechanisms may be provided to vary the capacitance effect between the tuning sleeve 177 and the shields as well. By varying the capacitance, the catheter's effective impedance can be effectively controlled.

In yet another preferred embodiment, a pair of back to back coaxial tuners are provided on the catheter transmission line. This embodiment effectively functions as a double stub tuner and is shown in shown in FIG. 12. In a preferred embodiment, the posts are spaced at three eighths of a wavelength and like the preceding embodiment, the tuner is located at an appropriate distance within a wavelength of the antenna junction. The structure of the coaxial tuners used in this embodiment may be similar to the capacitive tuner discussed above with respect to FIG. 11. However, in the particular embodiments shown in FIG. 12, a tuning slug 193 is positioned between each tuning sleeve 177 and the grounding shield 179. The tuning slug effectively shorts the ground shield 179 to the tuning sleeve 177 to control the catheter's effective impedance. In effect, ground shields 179 form a coaxial cable with tuning sleeve 177 having an impedance matched to the coaxial transmission line 53. In the embodiment shown in FIG. 12, push pull cables 191 are used to position the tuning slug relative to the tuning sleeve. Of course, again, a variety of alternative mechanisms may be provided to accomplish the desired tuning effect.

Figure 12:
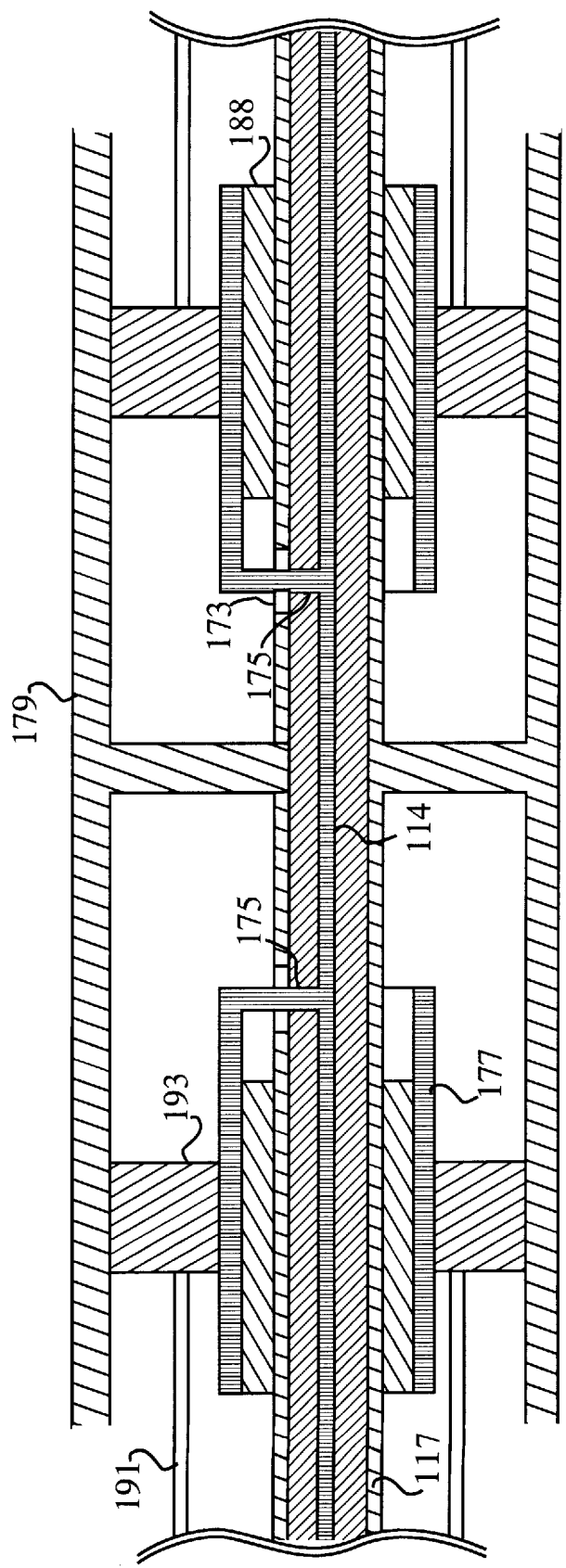
FIG. 12 is a diagrammatic cross sectional side view of a double co-axial capacitive tuner connected to the coaxial transmission line in accordance with another embodiment of the invention.

It should be appreciated that the proportional size of the tuning mechanism shown in FIGS. 11 and 12 have been greatly exaggerated in the diametric dimension in order to clearly show the various parts. In actuality, the entire capacitive tuner must be sized to fit within the central lumen in the outer tubing 51. Thus, the tuning sleeve will typically be relatively closely journaled around the shield with a good dielectric material 188 being placed therebetween. In some cases, the dielectric material may take the form of a dielectric film formed on the tuning sleeve or the shield.

Figure 13:
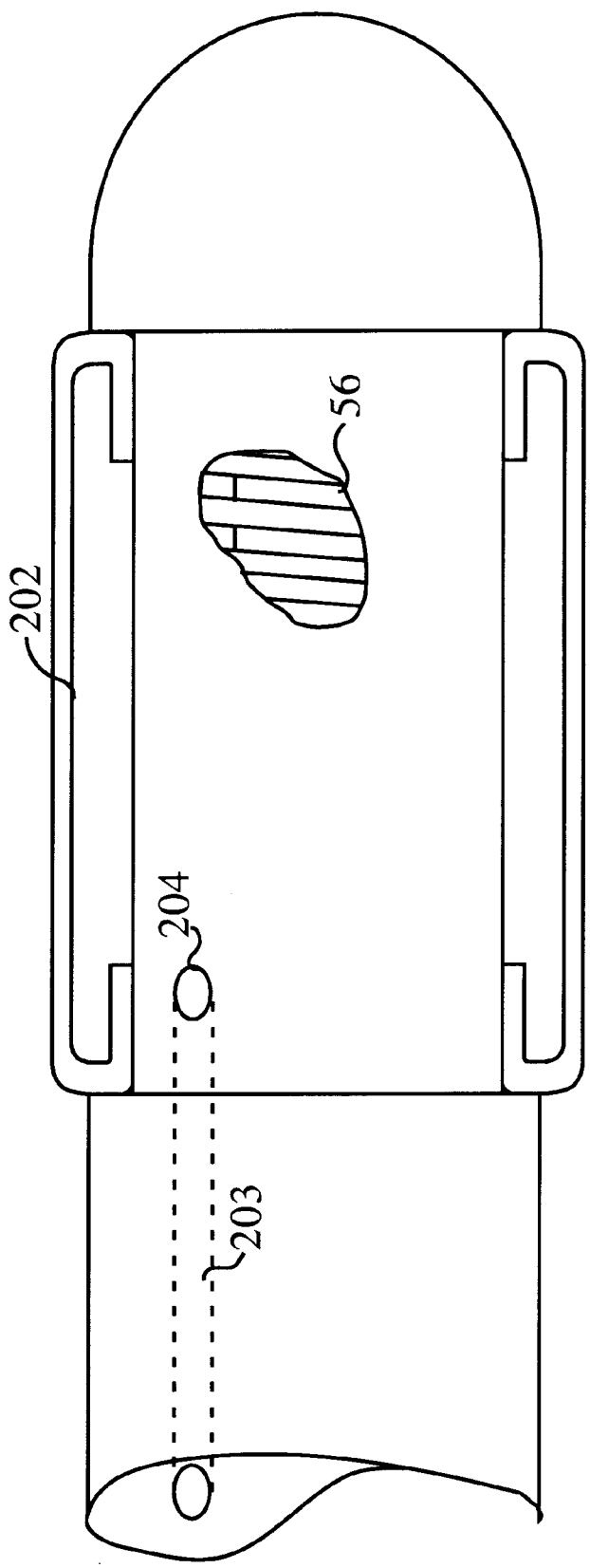
FIG. 13 is a diagrammatic partially cut away side view of the tip portion of an ablation catheter in accordance with another embodiment of the present invention that uses an inflatable balloon.

Referring next to FIG. 13, another embodiment of the invention will be described. In this embodiment, a conventional balloon 202 is journaled about the catheter tip in the region of the antenna coil 56. A fill port 204 in the shell 102 forms a connection between the interior of the balloon 202 and the distal end of a balloon feed lumen 203 similar to the feed tube 125 discussed above with reference to FIG. 8. To tune the antenna, a fluid dielectric is used to inflated (or deflate) the balloon 202.

Although only a few embodiments of the present invention have been described in detail, it should be understood that the present invention may be embodied in many other specific forms without departing from the spirit or scope of the invention. Particularly, the invention has been described in terms of an ablation catheter for cardiac applications, however, it should be appreciated that the described small diameter microwave ablation catheter could be used for a wide variety of alternative applications as well. Further, although a variety of antenna based tuning arrangements have been described in detail, it should be appreciated that many others that fall within the spirit and scope of this invention could be used as well. For example, the contact point of the center conductor with the helical antenna coil may be moved axially with respect to the helical coil by use of a sliding contact brush. Alternatively, the mechanical, electrical, capacitive, inductive, and/or resistive properties of any of the antenna components can also be used to aid in the tuning of the system. Further, in some circumstances, it may be desirable to provide a catheter with multiple tuning mechanisms to provide additionally flexibility.

Accordingly, the catheter design, the power supply design and the tuner design may all be modified within the scope of this invention. Therefore, the present examples are to be considered as illustrative and not restrictive, and the invention is not to be limited to the details given herein, but may be modified within the scope of the appended claims.

We claim:

1. A medical catheter system that includes a power supply having a microwave generator and microwave transmission means, a catheter having a microwave transmission line suitable for coupling to said transmission means and a microwave antenna for creating a microwave field, and a tuning system, the tuning system comprising:

a reflected power monitor arranged to monitor the amount of power that is reflected from the catheter during use; and a tuner arranged to facilitate dynamically matching the impedance of a power generator side portion of the catheter system with a catheter side portion of the catheter system during use of the catheter while microwave energy is being continuously delivered, the tuner being arranged to alter the effective impedance of a microwave energy transmitting portion of the catheter system during use of the catheter while microwave energy is being continuously delivered to compensate for variations in effective impedance that occur during use.

2. A medical catheter system that includes a power supply having a microwave generator and microwave transmission means, a catheter having a microwave transmission line suitable for coupling to said transmission means and a microwave antenna for creating a microwave field, and a tuning system, the tuning system comprising:

a reflected power monitor arranged to monitor the amount of power that is reflected from the catheter during use; and a tuner arranged to facilitate dynamically matching the impedance of a power generator side portion of the catheter system with a catheter side portion of the catheter system during use of the catheter while microwave energy is being continuously delivered, the tuner being arranged to alter the effective impedance of a microwave energy transmitting portion of the catheter system during use of the catheter while microwave energy is being continuously delivered to compensate for variations in effective impedance that occur while ablation is taking place.

3. A microwave ablation catheter system comprising:

an elongated catheter tubing having at least one lumen therein;

a coaxial microwave transmission line that passes through the lumen;

an insulated antenna carried at the distal end of the transmission line;

a microwave generator for generating microwave energy having a frequency in the range of approximately 800 MHz–3GHz;

transmission means for coupling the microwave generator to the coaxial transmission line;

a tuner arranged for dynamically matching the impedance of a microwave generator side portion of the catheter system with a catheter side portion of the catheter system while microwave energy is being continuously delivered and ablation is taking place, wherein tuning is accomplished by altering the effective impedance of one of said transmission means, said antenna and said coaxial transmission line; and a monitor arranged to monitor the amount of power transmitted to and reflected from the catheter side portion of the ablation catheter system while ablation is taking place, wherein indicia of the transmitted and reflected power are available to facilitate tuning using said tuner.

4. A microwave ablation catheter system as recited in claim 3 wherein the tuner is responsive to the power monitor and automatically matches the impedance of the power generator side portion of the catheter system with a catheter side portion of the catheter system while ablation is taking place.

5. A microwave ablation catheter system as recited in claim 3 further comprising:

an interlock system for automatically shutting off the microwave energy generator when certain predefined safety hazards are detected; and a display for displaying an indication of the magnitude of the reflected power, wherein the power monitoring means includes a pair of directional couplers and a pair of power sensors.

6. A catheter system comprising:

an elongated tubular member suitable for insertion into a vessel in the body of a patient, the tubular member having at least one lumen therein;

a coaxial catheter waveguide received in the lumen;

an electromagnetic energy generator;

transmission means for coupling the electromagnetic energy generator to the catheter waveguide, an antenna carried by the waveguide for generating an electromagnetic field when electromagnetic energy produced by said generator is applied thereto via the transmission means and the waveguide, whereby the electromagnetic field may be used for interventional medical procedures, the elongated tubular member, the waveguide and the antenna cooperating to form a catheter;

a reflected power monitor arranged to continuously monitor the electromagnetic energy that is reflected from the catheter during use and outputting a signal indicative of the reflected power; and a tuner for adjusting the impedance of a component of the catheter system while microwave energy is being continuously delivered, whereby the tuning means is suitable for use to reduce the reflected power that occurs during use of the catheter system in an interventional medical procedure, the tuner means being arranged to facilitate impedance matching of the catheter system while microwave energy is being continuously delivered and ablation is taking place.

7. A medical catheter system that includes a power supply having a microwave generator and microwave transmission means, a catheter having a microwave transmission line suitable for coupling to said transmission means and a microwave antenna for creating a microwave field, and a tuning system, the tuning system comprising:

a reflected power monitor arranged to continuously monitor the amount of power that is reflected from the catheter during use; and a tuner arranged to facilitate matching the impedance of a power generator side portion of the catheter system with a catheter side portion of the catheter system while microwave energy is being continuously delivered, based at least in part upon the continuously monitored reflected power, the tuner being arranged to alter the effective impedance of a microwave energy transmitting portion of the catheter system while microwave energy is being continuously delivered and ablation is taking place.

8. A medical catheter system that includes a power supply having a microwave generator and microwave transmission means, a catheter having a microwave transmission line suitable for coupling to said transmission means and a microwave antenna for creating a microwave field, and a tuning system, the tuning system comprising:

a reflected power monitor arranged to continuously monitor the amount of power that is reflected from the catheter during use; and a tuner arranged to facilitate periodic matching the impedance of a power generator side portion of the catheter system with a catheter side portion of the catheter system while microwave energy is being continuously delivered and an ablation procedure is taking place, the tuner being arranged to alter the effective impedance of a microwave energy transmitting portion of the catheter system while microwave energy is being continuously delivered and ablation is taking place to compensate for variations in effective impedance that occur during the ablation procedure.

9. A medical catheter system as recited in claim 8 wherein the tuner is responsive to changes in the power reflected from the catheter while ablation is taking place and automatically matches the impedance of the power generator side portion of the catheter system with a catheter side portion of the catheter system.

10. A microwave ablation catheter system comprising:

an elongated catheter tubing having at least one lumen therein;

a coaxial microwave transmission line that passes through the lumen;

an insulated antenna carried at the distal end of the transmission line;

a microwave generator for generating microwave energy having a frequency in the range of approximately 800 MHz –3 GHz;

transmission means for coupling the microwave generator to the coaxial transmission line, a tuner arranged for periodically matching the impedance of a microwave generator side portion of the catheter system with a catheter side portion of the catheter system while microwave energy is being continuously delivered and ablation is taking place, wherein tuning is accomplished by altering the effective impedance of one of said transmission means, said antenna and said coaxial transmission line; and a monitor arranged to continuously monitor the amount of power transmitted to and reflected from the catheter side portion of the ablation catheter system while ablation is taking place, wherein indicia of the transmitted and reflected power are available to facilitate tuning using said tuner.

11. A microwave ablation catheter system as recited in claim 10 wherein the tuner is responsive to the power monitor means and automatically matches the impedance of the power generator side portion of the catheter system with a catheter side portion of the catheter system during use of the catheter system.

12. A microwave ablation catheter system that includes an ablation catheter having a waveguide that takes the form of a coaxial cable and an antenna carried by the waveguide, the ablation catheter being coupled to a power supply by a connector arrangement, the power supply comprising:

a microwave energy generator for generating electromagnetic energy having a frequency in the microwave range, the microwave energy generator being coupled to the catheter waveguide through a coaxial transmission line and said connector;

a reflected power monitor including a directional coupler in communication with one of said catheter waveguide and said transmission line, for diverting a small portion of the power that is reflected from the catheter during use and outputting a signal indicative of the reflected power; and a tuner in communication with one of said transmission line, said catheter waveguide and said antenna, the tuner being arranged to facilitate matching the impedance of a power generator side portion of the catheter system with the impedance of a catheter side portion of the catheter system while microwave energy is being continuously delivered and ablation is taking place, whereby the output signal indicative of the reflected power is available for use in adjusting the tuner to minimize reflected power.

13. A power supply as recited in claim 12 wherein:

the tuner includes a manually adjustable control knob that can be accessed by a user to manually adjust the impedance of the catheter side portion of the catheter system; and the reflected power monitor further includes a display for displaying an indicia indicative of the reflected power to the user to facilitate manual adjustment of the control knob, the indicia being based at least in part on the output signal.

14. A power supply as recited in claim 12 wherein:

the tuner automatically matches the impedance of the power generator side portion of the catheter system with a catheter side portion of the catheter system; and the tuner further includes a tuner controller that receives the signal indicative of the reflected power from the reflected power monitor and generates a control signal based at least in part on the signal indicative of the reflected power.

15. A power supply as recited in claim 12 wherein tuner includes a stub tuner coupled to the transmission line for impedance matching of the power supply portion of the catheter system to the catheter side portion of the catheter system.

16. A power supply as recited in claim 12 further comprising a display that receives said signal for providing the user with an indication of the magnitude of the reflected power.

17. A power supply as recited in claim 12 further comprising an interlock system for automatically shutting off the microwave energy generator when certain predefined safety hazards are detected.

18. A power supply as recited in claim 17 wherein the interlock system shuts off the energy generator when no catheter is plugged into the power supply.

19. A power supply as recited in claim 17 for use in an ablation catheter system having means for monitoring the temperature in the region of the catheter tip, wherein the interlock system shuts off the microwave energy generator when an inappropriate thermal temperature is detected in the region of the catheter tip.

20. A power supply as recited in claim 17 wherein the interlock system shuts off the microwave generator when an abnormal increase in reflected power is detected by the reflected power monitor.

21. A power supply as recited in claim 17 wherein the interlock system shuts off the microwave generator when a short or open circuit is detected in an electrical component.

22. A power supply as recited in claim 12 further comprising a transmitted power monitor for monitoring the amount of power transmitted to the catheter during use.

23. A medical microwave ablation catheter system that includes an ablation catheter having a coaxial transmission waveguide and an antenna coupled to the coaxial transmission waveguide for radiating microwave energy, the coaxial transmission waveguide being coupled to a power supply by a connector arrangement, the power supply comprising:

a microwave generator for generating electromagnetic energy having a frequency in the microwave range, the microwave energy generator being coupled to the coaxial transmission waveguide through a coaxial power supply transmission line and said connector;

a monitor arranged to monitor the amount of power that is transmitted to and reflected from the catheter while ablation is taking place, the monitoring means including, a first directional coupler in communication with the transmission line for diverting a small portion of the power that is reflected from the catheter while ablation is taking place, a first power sensor for detecting the magnitude of the power diverted by the first directional coupler and outputting a first signal indicative of the magnitude of the power that is reflected from the catheter while ablation is taking place, a second directional coupler in communication with the transmission line for diverting a small portion of the power that is transmitted to the catheter while ablation is taking place, and a second power sensor for detecting the magnitude of the power diverted by the second directional coupler and outputting a second signal indicative of the magnitude of the power that is transmitted to the catheter while ablation is taking place;

a detector arranged to detect the temperature in the vicinity of the antenna portion of the ablation catheter;

a tuner arranged to automatically match the impedance of a power generator side portion of the catheter system with the impedance of a catheter side portion of the catheter system while ablation is taking place, the tuner including, a tuner controller that receives said first and second signals and generates a control signal based at least in part on the magnitude of the reflected power, and a stub tuning mechanism coupled to the transmission line for adjusting the impedance of the transmission line while microwave energy is being continuously delivered, the stub tuning mechanism being responsive to said control signal, whereby the tuner is arranged to match the impedance of the power generator side portion of the catheter system with the impedance of the catheter side portion of the catheter system at least in part by using the stub tuning mechanism to alter the effective impedance of the transmission line while microwave energy is being continuously delivered; and an interlock system for automatically shutting off the microwave generator when certain predefined safety hazards are detected, the predetermined safety hazards including when no catheter is plugged into the power supply and when an over temperature condition is detected, the interlock system being in communication with the temperature detector.

* * * * *